United States Patent
Kaneko et al.

[11] Patent Number: 5,965,442
[45] Date of Patent: Oct. 12, 1999

[54] METHOD OF ALTERING ENZYMES AND A NOVEL NEOPULLULANASE

[75] Inventors: Hiroki Kaneko; Toshikazu Takada; Jiro Shimada, all of Tokyo; Takashi Kuriki, Osaka; Michiyo Yanase, Osaka; Hiroki Takata, Osaka; Shigetaka Okada, Osaka, all of Japan

[73] Assignees: NEC Corporation, Tokyo; Ezaki Glico Kabushiki Kaisha, Osaka, both of Japan

[21] Appl. No.: 08/339,715

[22] Filed: Nov. 14, 1994

[30] Foreign Application Priority Data

Nov. 12, 1993 [JP] Japan .................................. 5-306096

[51] Int. Cl.$^6$ .......................... C12N 15/11; C12N 15/54; C12N 15/56; C12N 15/70
[52] U.S. Cl. ........................ 435/471; 435/69.1; 435/193; 435/201; 435/210; 435/252.3; 435/320.1; 435/476; 536/23.2
[58] Field of Search .................................. 435/15, 172.3, 435/69.1, 172.1, 320.1, 201, 210, 252.3, 471, 476; 536/23.2

[56] References Cited

U.S. PATENT DOCUMENTS

| | | | |
|---|---|---|---|
| 4,853,871 | 8/1989 | Pantoliano et al. | 364/496 |
| 5,162,210 | 11/1992 | Sierks et al. | 435/96 |
| 5,166,741 | 11/1992 | Bryan et al. | 435/87 |
| 5,352,594 | 10/1994 | Poulouse | 435/172.1 |

OTHER PUBLICATIONS

Kuriki, T., et al., Journal of Bacteriology, vol. 173, "Analysis of the active center of Bacillus stearothermophilus neopullulanase", pp. 6147–6152, 1991.

"Action of Neopullulanase," *J. Biol. Chem.* 267:18447–18452 (Sep. 15, 1992).

Rastetter (1983) Trends Biotech 1:80–84. "Enzyme engineering: applications and promise".

Lamminmäki et al (1996) Bioc. Biop. Acta 1295:195–200. "Structual consequences of neopullulanase mutations".

Matsui et al (1994) Biochem 33:451–458 "Roles of the aromatic residues conserved in the active center of Saccharomycopsis α–anylase for transglycosylation and Hydrolysis Activity".

Kuriki et al (1996) JBC 271:17321–17329 "Controlling substrate preference and transglycosylation activity of neopullulanase by manipulating steric constraint . . . ".

Mosimann et al (1995) proteins: structure, function and genetics 23:301–317 "A critical assessment of comparative molecular modeling of tertiary structure of proteins".

"Hydrophobic parameters of π of amino–acid side chains from the partitioning of N–acetyl–amino–acid amides," Jean–Luc Fauchere, et al., Eur. J. Med. Chem. —Chim. Ther., 1983–18, No. 4, pp. 369–375.

*Primary Examiner*—Robert A. Wax
*Assistant Examiner*—William W. Moore
*Attorney, Agent, or Firm*—Young & Thompson

[57] ABSTRACT

An enzyme is altered by introducing an additional hydrophobic group to enhance the hydrophobic environment in the enzyme so as to interfere with entrance of a water molecule. In this connection, the site of introduction and kind of hydrophobic group to be introduced are selected on the basis of comprehensive analysis of amino acid sequence, three-dimensional structure, reaction mechanism or the like of the target enzyme. Using this method, an amino acid residue of neopullulanase derived from *Bacillus stearothermophilus* was replaced by another amino acid.

12 Claims, 8 Drawing Sheets

T.P.: MRKEAIYHRPADNFAYAYDSETLHLRLRTKKDDIDRVELLHGDPYDWQNGAWQFQMMPMR

R.P.: ----------

KTGSDELFDYWFAEVKPPYYRRLRYGFVLYSGEEKLVYTEKGFYFEVPTDDTAYYFCFPFL

----------

HRVDLFEAPDWVKDTVWYQIFPERFANGNPSISPEGSRPWGSEDPTPTSFFGGDLQGIID
------ATPADWRSQSIYFLLTDRFARTDGSTTATCN----------TADQKYCGGTWQGIID

HLDYLVDLGITGIYLTPIFRSPSNH----------KYDTADYFEVDPHFGDKETLKTLIDRC
KLDYIQGMGFTAIWITPVTAQLPQDCAYGDAYTGYWQTDIYSLNENYGTADDLKALSSAL

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 588 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Met Arg Lys Glu Ala Ile Tyr His Arg Pro Ala Asp Asn Phe Ala Tyr
1               5                   10                  15

Ala Tyr Asp Ser Glu Thr Leu His Leu Arg Leu Arg Thr Lys Lys Asp
                20                  25                  30

Asp Ile Asp Arg Val Glu Leu Leu His Gly Asp Pro Tyr Asp Trp Gln
            35                  40                  45

Asn Gly Ala Trp Gln Phe Gln Met Met Pro Met Arg Lys Thr Gly Ser
        50                  55                  60

Asp Glu Leu Phe Asp Tyr Trp Phe Ala Glu Val Lys Pro Pro Tyr Arg
65                  70                  75                  80

Arg Leu Arg Tyr Gly Phe Val Leu Tyr Ser Gly Glu Glu Lys Leu Val
                85                  90                  95

Tyr Thr Glu Lys Gly Phe Tyr Phe Glu Val Pro Thr Asp Asp Thr Ala
                100                 105                 110

Tyr Tyr Phe Cys Phe Pro Phe Leu His Arg Val Asp Leu Phe Glu Ala
            115                 120                 125

Pro Asp Trp Val Lys Asp Thr Val Trp Tyr Gln Ile Phe Pro Glu Arg
        130                 135                 140

Phe Ala Asn Gly Asn Pro Ser Ile Ser Pro Glu Gly Ser Arg Pro Trp
145                 150                 155                 160

Gly Ser Glu Asp Pro Thr Pro Thr Ser Phe Phe Gly Gly Asp Leu Gln
                165                 170                 175

Gly Ile Ile Asp His Leu Asp Tyr Leu Val Asp Leu Gly Ile Thr Gly
                180                 185                 190

Ile Tyr Leu Thr Pro Ile Phe Arg Ser Pro Ser Asn His Lys Tyr Asp
            195                 200                 205

Thr Ala Asp Tyr Phe Glu Val Asp Pro His Phe Gly Asp Lys Glu Thr
        210                 215                 220

Leu Lys Thr Leu Ile Asp Arg Cys His Glu Lys Gly Ile Arg Val Met
225                 230                 235                 240

Leu Asp Ala Val Phe Asn His Cys Gly Tyr Glu Phe Ala Pro Phe Gln
                245                 250                 255
```

-continued

Asp Val Trp Lys Asn Gly Glu Ser Ser Lys Tyr Lys Asp Trp Phe His
            260                 265                 270

Ile His Glu Phe Pro Leu Gln Thr Glu Pro Arg Pro Asn Tyr Asp Thr
            275                 280                 285

Phe Arg Phe Val Pro Gln Met Pro Lys Leu Asn Thr Ala Asn Pro Glu
290                 295                 300

Val Lys Arg Tyr Leu Leu Asp Val Ala Thr Tyr Trp Ile Arg Glu Phe
305                 310                 315                 320

Asp Ile Asp Gly Trp Arg Leu Asp Val Ala Asn Glu Ile Asp His Glu
                325                 330                 335

Phe Trp Arg Glu Phe Arg Gln Glu Val Lys Ala Leu Lys Pro Asp Val
            340                 345                 350

Tyr Ile Leu Gly Glu Ile Trp His Asp Ala Met Pro Trp Leu Arg Gly
            355                 360                 365

Asp Gln Phe Asp Ala Val Met Asn Tyr Pro Phe Thr Asp Gly Val Leu
370                 375                 380

Arg Phe Phe Ala Lys Glu Glu Ile Ser Ala Arg Gln Phe Ala Asn Gln
385                 390                 395                 400

Met Met His Val Leu His Ser Tyr Pro Asn Asn Val Asn Glu Ala Ala
                405                 410                 415

Phe Asn Leu Leu Gly Ser His Asp Thr Ser Arg Ile Leu Thr Val Cys
            420                 425                 430

Gly Gly Asp Ile Arg Lys Val Lys Leu Leu Phe Leu Phe Gln Leu Thr
            435                 440                 445

Phe Thr Gly Ser Pro Cys Ile Tyr Tyr Gly Asp Glu Ile Gly Met Thr
450                 455                 460

Gly Gly Asn Asp Pro Glu Cys Arg Lys Cys Met Val Trp Asp Pro Met
465                 470                 475                 480

Gln Gln Asn Lys Glu Leu His Gln His Val Lys Gln Leu Ile Ala Leu
            485                 490                 495

Arg Lys Gln Tyr Arg Ser Leu Arg Arg Gly Glu Ile Ser Phe Leu His
            500                 505                 510

Ala Asp Asp Glu Met Asn Tyr Leu Ile Tyr Lys Lys Thr Asp Gly Asp
            515                 520                 525

Glu Thr Val Leu Val Ile Ile Asn Arg Ser Asp Gln Lys Ala Asp Ile
530                 535                 540

Pro Ile Pro Leu Asp Ala Arg Gly Thr Trp Leu Val Asn Leu Leu Thr
545                 550                 555                 560

Gly Glu Arg Phe Ala Ala Glu Ala Gly Thr Leu Cys Thr Ser Leu Pro
                565                 570                 575

Pro Tyr Gly Phe Val Leu Tyr Ala Ile Glu His Trp
            580                 585

(2) INFORMATION FOR SEQ ID NO:2:

(i) SEQUENCE CHARACTERISTICS:
        (A) LENGTH: 478 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr

-continued

```
                    20                  25                  30
Ala Asp Gln Lys Tyr Cys Gly Thr Trp Gln Gly Ile Ile Asp Lys
                35                  40                  45
Leu Asp Tyr Ile Gln Gly Met Gly Phe Thr Ala Ile Trp Ile Thr Pro
 50                          55                  60
Val Thr Ala Gln Leu Pro Gln Asp Cys Ala Tyr Gly Asp Ala Tyr Thr
 65                  70                  75                  80
Gly Tyr Trp Gln Thr Asp Ile Tyr Ser Leu Asn Glu Asn Tyr Gly Thr
                85                  90                  95
Ala Asp Asp Leu Lys Ala Leu Ser Ser Ala Leu His Glu Arg Gly Met
                100                 105                 110
Tyr Leu Met Val Asp Val Val Ala Asn His Met Gly Tyr Asp Gly Ala
                115                 120                 125
Gly Ser Ser Val Asp Tyr Ser Val Phe Lys Pro Phe Ser Ser Gln Asp
 130                 135                 140
Tyr Phe His Pro Phe Cys Phe Ile Gln Asn Tyr Glu Asp Gln Thr Gln
 145                 150                 155                 160
Val Glu Asp Cys Trp Leu Gly Asp Asn Thr Val Ser Leu Pro Asp Leu
                165                 170                 175
Asp Thr Thr Lys Asp Val Val Lys Asn Glu Trp Tyr Asp Trp Val Gly
                180                 185                 190
Ser Leu Val Ser Asn Tyr Ser Ile Asp Gly Leu Arg Ile Asp Thr Val
                195                 200                 205
Lys His Val Gln Lys Asp Phe Trp Pro Gly Tyr Asn Lys Ala Ala Gly
                210                 215                 220
Val Tyr Cys Ile Gly Glu Val Leu Asp Gly Asp Pro Ala Tyr Thr Cys
 225                 230                 235                 240
Pro Tyr Gln Asn Val Met Asp Gly Val Leu Asn Tyr Pro Ile Tyr Tyr
                245                 250                 255
Pro Leu Leu Asn Ala Phe Lys Ser Thr Ser Gly Ser Met Asp Asp Leu
                260                 265                 270
Tyr Asn Met Ile Asn Thr Val Lys Ser Asp Cys Pro Asp Ser Thr Leu
                275                 280                 285
Leu Gly Thr Phe Val Glu Asn His Asp Asn Pro Arg Phe Ala Ser Tyr
 290                 295                 300
Thr Asn Asp Ile Ala Leu Ala Lys Asn Val Ala Ala Phe Ile Ile Leu
 305                 310                 315                 320
Asn Asp Gly Leu Pro Ile Ile Tyr Ala Gly Gln Glu Gln His Tyr Ala
                325                 330                 335
Gly Gly Asn Asp Pro Ala Asn Arg Glu Ala Thr Trp Leu Ser Gly Tyr
                340                 345                 350
Pro Thr Asp Ser Glu Leu Tyr Lys Leu Ile Ala Ser Ala Asn Ala Ile
                355                 360                 365
Arg Asn Tyr Ala Ile Ser Lys Asp Thr Gly Phe Val Thr Tyr Lys Asn
 370                 375                 380
Pro Tyr Ile Lys Asp Asp Thr Ile Ala Met Arg Lys Gly Thr Asp
 385                 390                 395                 400
Gly Ser Gln Ile Val Thr Ile Leu Ser Asn Lys Gly Ala Ser Gly Asp
                405                 410                 415
Ser Tyr Thr Leu Ser Leu Ser Gly Ala Ser Tyr Thr Ala Gly Gln Gln
                420                 425                 430
Leu Thr Glu Val Ile Gly Cys Thr Thr Val Thr Val Gly Ser Asp Gly
                435                 440                 445
```

-continued

Asn Val Pro Val Pro Met Ala Gly Gly Leu Pro Arg Val Leu Tyr Pro
    450                 455                 460

Thr Glu Lys Leu Ala Gly Ser Lys Ile Cys Ser Asp Ser Ser
465                 470                 475

(2) INFORMATION FOR SEQ ID NO:3:

(i) SEQUENCE CHARACTERISTICS:
        (A) LENGTH: 588 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Arg Lys Glu Ala Ile Tyr His Arg Pro Ala Asp Asn Phe Ala Tyr
1               5                   10                  15

Ala Tyr Asp Ser Glu Thr Leu His Leu Arg Leu Arg Thr Lys Lys Asp
                20                  25                  30

Asp Ile Asp Arg Val Glu Leu Leu His Gly Asp Pro Tyr Asp Trp Gln
            35                  40                  45

Asn Gly Ala Trp Gln Phe Gln Met Met Pro Met Arg Lys Thr Gly Ser
50                  55                  60

Asp Glu Leu Phe Asp Tyr Trp Phe Ala Glu Val Lys Pro Pro Tyr Arg
65                  70                  75                  80

Arg Leu Arg Tyr Gly Phe Val Leu Tyr Ser Gly Glu Glu Lys Leu Val
                85                  90                  95

Tyr Thr Glu Lys Gly Phe Tyr Phe Glu Val Pro Thr Asp Asp Thr Ala
                100                 105                 110

Tyr Tyr Phe Cys Phe Pro Phe Leu His Arg Val Asp Leu Phe Glu Ala
            115                 120                 125

Pro Asp Trp Val Lys Asp Thr Val Trp Tyr Gln Ile Phe Pro Glu Arg
        130                 135                 140

Phe Ala Asn Gly Asn Pro Ser Ile Ser Pro Glu Gly Ser Arg Pro Trp
145                 150                 155                 160

Gly Ser Glu Asp Pro Thr Pro Thr Ser Phe Phe Gly Gly Asp Leu Gln
                165                 170                 175

Gly Ile Ile Asp His Leu Asp Tyr Leu Val Asp Leu Gly Ile Thr Gly
            180                 185                 190

Ile Tyr Leu Thr Pro Ile Phe Arg Ser Pro Ser Asn His Lys Tyr Asp
        195                 200                 205

Thr Ala Asp Tyr Phe Glu Val Asp Pro His Phe Gly Asp Lys Glu Thr
210                 215                 220

Leu Lys Thr Leu Ile Asp Arg Cys His Glu Lys Gly Ile Arg Val Met
225                 230                 235                 240

Leu Asp Ala Val Phe Asn His Cys Gly Tyr Glu Phe Ala Pro Phe Gln
                245                 250                 255

Asp Val Trp Lys Asn Gly Glu Ser Ser Lys Tyr Lys Asp Trp Phe His
            260                 265                 270

Ile His Glu Phe Pro Leu Gln Thr Glu Pro Arg Pro Asn Tyr Asp Thr
        275                 280                 285

Phe Arg Phe Val Pro Gln Met Pro Lys Leu Asn Thr Ala Asn Pro Glu
290                 295                 300

Val Lys Arg Tyr Leu Leu Asp Val Ala Thr Tyr Trp Ile Arg Glu Phe
305                 310                 315                 320

Asp Ile Asp Gly Trp Arg Leu Asp Val Ala Asn Glu Ile Asp His Glu

```
                        325                 330                 335
Phe Trp Arg Glu Phe Arg Gln Glu Val Lys Ala Leu Lys Pro Asp Val
                340                 345                 350
Tyr Ile Leu Gly Glu Ile Trp His Asp Ala Met Pro Trp Leu Arg Gly
                355                 360                 365
Asp Gln Phe Asp Ala Val Met Asn Phe Pro Phe Thr Asp Gly Val Leu
        370                 375                 380
Arg Phe Phe Ala Lys Glu Glu Ile Ser Ala Arg Gln Phe Ala Asn Gln
385                 390                 395                 400
Met Met His Val Leu His Ser Tyr Pro Asn Asn Val Asn Glu Ala Ala
                405                 410                 415
Phe Asn Leu Leu Gly Ser His Asp Thr Ser Arg Ile Leu Thr Val Cys
                420                 425                 430
Gly Gly Asp Ile Arg Lys Val Lys Leu Leu Phe Leu Phe Gln Leu Thr
            435                 440                 445
Phe Thr Gly Ser Pro Cys Ile Tyr Tyr Gly Asp Glu Ile Gly Met Thr
            450                 455                 460
Gly Gly Asn Asp Pro Glu Cys Arg Lys Cys Met Val Trp Asp Pro Met
465                 470                 475                 480
Gln Gln Asn Lys Glu Leu His Gln His Val Lys Gln Leu Ile Ala Leu
                485                 490                 495
Arg Lys Gln Tyr Arg Ser Leu Arg Arg Gly Glu Ile Ser Phe Leu His
                500                 505                 510
Ala Asp Asp Glu Met Asn Tyr Leu Ile Tyr Lys Lys Thr Asp Gly Asp
            515                 520                 525
Glu Thr Val Leu Val Ile Ile Asn Arg Ser Asp Gln Lys Ala Asp Ile
            530                 535                 540
Pro Ile Pro Leu Asp Ala Arg Gly Thr Trp Leu Val Asn Leu Leu Thr
545                 550                 555                 560
Gly Glu Arg Phe Ala Ala Glu Ala Glu Thr Leu Cys Thr Ser Leu Pro
                565                 570                 575
Pro Tyr Gly Phe Val Leu Tyr Ala Ile Glu His Trp
            580                 585

(2) INFORMATION FOR SEQ ID NO:4:

(i) SEQUENCE CHARACTERISTICS:
        (A) LENGTH: 588 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Met Arg Lys Glu Ala Ile Tyr His Arg Pro Ala Asp Asn Phe Ala Tyr
1               5                   10                  15

Ala Tyr Asp Ser Glu Thr Leu His Leu Arg Leu Arg Thr Lys Lys Asp
                20                  25                  30

Asp Ile Asp Arg Val Glu Leu Leu His Gly Asp Pro Tyr Asp Trp Gln
            35                  40                  45

Asn Gly Ala Trp Gln Phe Gln Met Met Pro Met Arg Lys Thr Gly Ser
        50                  55                  60

Asp Glu Leu Phe Asp Tyr Trp Phe Ala Glu Val Lys Pro Pro Tyr Arg
65                  70                  75                  80

Arg Leu Arg Tyr Gly Phe Val Leu Tyr Ser Gly Glu Glu Lys Leu Val
                85                  90                  95
```

```
Tyr Thr Glu Lys Gly Phe Tyr Phe Glu Val Pro Thr Asp Asp Thr Ala
            100                 105                 110
Tyr Tyr Phe Cys Phe Pro Phe Leu His Arg Val Asp Leu Phe Glu Ala
            115                 120                 125
Pro Asp Trp Val Lys Asp Thr Val Trp Tyr Gln Ile Phe Pro Glu Arg
130                 135                 140
Phe Ala Asn Gly Asn Pro Ser Ile Ser Pro Glu Gly Ser Arg Pro Trp
145                 150                 155                 160
Gly Ser Glu Asp Pro Thr Pro Thr Ser Phe Phe Gly Gly Asp Leu Gln
                165                 170                 175
Gly Ile Ile Asp His Leu Asp Tyr Leu Val Asp Leu Gly Ile Thr Gly
                180                 185                 190
Ile Tyr Leu Thr Pro Ile Phe Arg Ser Pro Ser Asn His Lys Tyr Asp
        195                 200                 205
Thr Ala Asp Tyr Phe Glu Val Asp Pro His Phe Gly Asp Lys Glu Thr
210                 215                 220
Leu Lys Thr Leu Ile Asp Arg Cys His Glu Lys Gly Ile Arg Val Met
225                 230                 235                 240
Leu Asp Ala Val Phe Asn His Cys Gly Tyr Glu Phe Ala Pro Phe Gln
                245                 250                 255
Asp Val Trp Lys Asn Gly Glu Ser Ser Lys Tyr Lys Asp Trp Phe His
                260                 265                 270
Ile His Glu Phe Pro Leu Gln Thr Glu Pro Arg Pro Asn Tyr Asp Thr
        275                 280                 285
Phe Arg Phe Val Pro Gln Met Pro Lys Leu Asn Thr Ala Asn Pro Glu
    290                 295                 300
Val Lys Arg Tyr Leu Leu Asp Val Ala Thr Tyr Trp Ile Arg Glu Phe
305                 310                 315                 320
Asp Ile Asp Gly Trp Arg Leu Asp Val Ala Asn Glu Ile Asp His Glu
                325                 330                 335
Phe Trp Arg Glu Phe Arg Gln Glu Val Lys Ala Leu Lys Pro Asp Val
                340                 345                 350
Tyr Ile Leu Gly Glu Ile Trp His Asp Ala Met Pro Trp Leu Arg Gly
            355                 360                 365
Asp Gln Phe Asp Ala Val Met Asn Tyr Pro Phe Thr Asp Gly Val Leu
    370                 375                 380
Arg Phe Phe Ala Lys Glu Glu Ile Ser Ala Arg Gln Phe Ala Asn Gln
385                 390                 395                 400
Met Met His Val Leu His Ser Tyr Pro Asn Asn Val Asn Glu Ala Ala
                405                 410                 415
Phe Asn Leu Leu Gly Val His Asp Thr Ser Arg Ile Leu Thr Val Cys
            420                 425                 430
Gly Gly Asp Ile Arg Lys Val Lys Leu Leu Phe Leu Phe Gln Leu Thr
        435                 440                 445
Phe Thr Gly Ser Pro Cys Ile Tyr Tyr Gly Asp Glu Ile Gly Met Thr
    450                 455                 460
Gly Gly Asn Asp Pro Glu Cys Arg Lys Cys Met Val Trp Asp Pro Met
465                 470                 475                 480
Gln Gln Asn Lys Glu Leu His Gln His Val Lys Gln Leu Ile Ala Leu
                485                 490                 495
Arg Lys Gln Tyr Arg Ser Leu Arg Gly Glu Ile Ser Phe Leu His
            500                 505                 510
Ala Asp Asp Glu Met Asn Tyr Leu Ile Tyr Lys Lys Thr Asp Gly Asp
```

-continued

```
                515                 520                 525
Glu Thr Val Leu Val Ile Ile Asn Arg Ser Asp Gln Lys Ala Asp Ile
    530                 535                 540

Pro Ile Pro Leu Asp Ala Arg Gly Thr Trp Leu Val Asn Leu Leu Thr
545                 550                 555                 560

Gly Glu Arg Phe Ala Ala Glu Ala Glu Thr Leu Cys Thr Ser Leu Pro
                565                 570                 575

Pro Tyr Gly Phe Val Leu Tyr Ala Ile Glu His Trp
                580                 585
```

(2) INFORMATION FOR SEQ ID NO:5:

(i) SEQUENCE CHARACTERISTICS:
        (A) LENGTH: 588 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Arg Lys Glu Ala Ile Tyr His Arg Pro Ala Asp Asn Phe Ala Tyr
1               5                   10                  15

Ala Tyr Asp Ser Glu Thr Leu His Leu Arg Leu Arg Thr Lys Lys Asp
                20                  25                  30

Asp Ile Asp Arg Val Glu Leu Leu His Gly Asp Pro Tyr Asp Trp Gln
            35                  40                  45

Asn Gly Ala Trp Gln Phe Gln Met Met Pro Met Arg Lys Thr Gly Ser
50                  55                  60

Asp Glu Leu Phe Asp Tyr Trp Phe Ala Glu Val Lys Pro Pro Tyr Arg
65                  70                  75                  80

Arg Leu Arg Tyr Gly Phe Val Leu Tyr Ser Gly Glu Glu Lys Leu Val
                85                  90                  95

Tyr Thr Glu Lys Gly Phe Tyr Phe Glu Val Pro Thr Asp Asp Thr Ala
                100                 105                 110

Tyr Tyr Phe Cys Phe Pro Phe Leu His Arg Val Asp Leu Phe Glu Ala
            115                 120                 125

Pro Asp Trp Val Lys Asp Thr Val Trp Tyr Gln Ile Phe Pro Glu Arg
        130                 135                 140

Phe Ala Asn Gly Asn Pro Ser Ile Ser Pro Glu Gly Ser Arg Pro Trp
145                 150                 155                 160

Gly Ser Glu Asp Pro Thr Pro Thr Ser Phe Phe Gly Gly Asp Leu Gln
                165                 170                 175

Gly Ile Ile Asp His Leu Asp Tyr Leu Val Asp Leu Gly Ile Thr Gly
            180                 185                 190

Ile Tyr Leu Thr Pro Ile Phe Arg Ser Pro Ser Asn His Lys Tyr Asp
        195                 200                 205

Thr Ala Asp Tyr Phe Glu Val Asp Pro His Phe Gly Asp Lys Glu Thr
    210                 215                 220

Leu Lys Thr Leu Ile Asp Arg Cys His Glu Lys Gly Ile Arg Val Met
225                 230                 235                 240

Leu Asp Ala Val Phe Asn His Cys Gly Tyr Glu Phe Ala Pro Phe Gln
                245                 250                 255

Asp Val Trp Lys Asn Gly Glu Ser Ser Lys Tyr Lys Asp Trp Phe His
                260                 265                 270

Ile His Glu Phe Pro Leu Gln Thr Glu Pro Arg Pro Asn Tyr Asp Thr
        275                 280                 285
```

Phe Arg Phe Val Pro Gln Met Pro Lys Leu Asn Thr Ala Asn Pro Glu
290                 295                 300

Val Lys Arg Tyr Leu Leu Asp Val Ala Thr Tyr Trp Ile Arg Glu Phe
305                 310                 315                 320

Asp Ile Asp Gly Trp Arg Leu Asp Val Ala Asn Glu Ile Asp His Glu
            325                 330                 335

Phe Trp Arg Glu Phe Arg Gln Glu Val Lys Ala Leu Lys Pro Asp Val
                340                 345                 350

Tyr Ile Leu Gly Glu Ile Trp His Asp Ala Met Pro Trp Leu Arg Gly
            355                 360                 365

Asp Gln Phe Asp Ala Val Leu Asn Tyr Pro Phe Thr Asp Gly Val Leu
370                 375                 380

Arg Phe Phe Ala Lys Glu Glu Ile Ser Ala Arg Gln Phe Ala Asn Gln
385                 390                 395                 400

Met Met His Val Leu His Ser Tyr Pro Asn Asn Val Asn Glu Ala Ala
            405                 410                 415

Phe Asn Leu Leu Gly Ser His Asp Thr Ser Arg Ile Leu Thr Val Cys
            420                 425                 430

Gly Gly Asp Ile Arg Lys Val Lys Leu Leu Phe Leu Phe Gln Leu Thr
            435                 440                 445

Phe Thr Gly Ser Pro Cys Ile Tyr Tyr Gly Asp Glu Ile Gly Met Thr
            450                 455                 460

Gly Gly Asn Asp Pro Glu Cys Arg Lys Cys Met Val Trp Asp Pro Met
465                 470                 475                 480

Gln Gln Asn Lys Glu Leu His Gln His Val Lys Gln Leu Ile Ala Leu
            485                 490                 495

Arg Lys Gln Tyr Arg Ser Leu Arg Arg Gly Glu Ile Ser Phe Leu His
            500                 505                 510

Ala Asp Asp Glu Met Asn Tyr Leu Ile Tyr Lys Lys Thr Asp Gly Asp
            515                 520                 525

Glu Thr Val Leu Val Ile Ile Asn Arg Ser Asp Gln Lys Ala Asp Ile
530                 535                 540

Pro Ile Pro Leu Asp Ala Arg Gly Thr Trp Leu Val Asn Leu Leu Thr
545                 550                 555                 560

Gly Glu Arg Phe Ala Ala Glu Ala Glu Thr Leu Cys Thr Ser Leu Pro
            565                 570                 575

Pro Tyr Gly Phe Val Leu Tyr Ala Ile Glu His Trp
            580                 585

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:6:

TTTAAGCTTT TTTCTACTGA ATTTG                                      25

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: Oligonucleotide (xi) SEQUENCE DESCRIPTION: SEQ ID NO:7:

TTTGCATGCA AAGAACGCTC GGG 23

METHOD OF ALTERING ENZYMES AND A NOVEL NEOPULLULANASE

BACKGROUND OF THE INVENTION

1. Field of the Invention

The present invention relates to a method of altering an enzyme, in particular, to a method of altering an enzyme to enhance its transfer reaction, and to a novel neopullulanase altered using said method.

2. Description of the Prior Art

Conventional methods used to enhance enzymatic transfer reactions are to change the external environment for enzyme reaction, for example, an enzyme reaction is carried out, not in an aqueous solution, but in an organic solvent. The reaction mechanism of a hydrolysis reaction and a transfer reaction are the same, in principle, in terms of an organic chemical reaction; a reaction is called hydrolysis when the acceptor is a water molecule, whereas it is called a transfer reaction when the acceptor is a compound other than water. Many transferases have catalytic activities for both hydrolytic and transfer reactions. Thus, the transfer reaction of such transferases can be enhanced by carrying out the enzyme reaction in an organic solvent so as to suppress the hydrolytic reaction.

In contrast, in order to enhance the transfer reaction an aqueous solution, it is necessary to alter an enzyme itself to increase its indigenous transfer activity. Genetic engineering and protein engineering are basic technologies to alter an enzymes itself to improve its characteristics for industrial use (e.g., stability, substrate specificity and reaction specificity). An example of the use of these technologies to improve the stability of a protein is described in Japanese Patent Laid-Open No. 224489/1985 in which additional cysteine residues are introduced into a native protein; these are linked via a disulfide bond, which increased the stability of the protein. In this connection, a method has been developed to determine a site to introduce the disulfide bonding using computer modeling (U.S. Pat. No. 4,853,871). Moreover, several other techniques to improve stability of proteins have been disclosed. Further, an example of altering the substrate specificity of an enzyme was given by some members of the present invention, in which they proposed alteration of the substrate specificity using protein engineering to obtain a novel dairy lactic acid bacterium protease having a substrate decomposing activity entirely different from that of the corresponding wild-type enzyme (Japanese Patent Application No. 190119/1992; Laid-Open No. 153945/1994). A novel protease having a specific activity higher than a corresponding natural-type enzyme was also disclosed in this Patent Application. Also, in Japanese Patent Laid-Open No. 20291/1992, some members of the present invention disclosed a neopullulanase in which its substrate specificity was altered by protein engineering technology.

It is known that the neopullulanase, used in the present invention, derived from *Bacillus stearothermophilus*, acts on polysaccharides and oligosaccharides, such as starch and pullulan, hydrolyzes the alpha-1,4- and alpha-1,6- glucosidic bonds, and forms alpha-1,4- and alpha-1,6- glucosidic bonds by sugar transfer reactions (J. Biol. Chem., 267, 18447–18452, 1992).

Of the conventional methods to enhance enzymatic transfer reactions, the method in which the enzyme reaction proceeds in an organic solvent cannot be applied to the food industry because of the toxicity of the organic solvent. Increased manufacturing costs by the use of an organic solvent is another problem.

On the other hand, of the conventional methods mentioned above, the method of altering the enzyme itself using protein engineering technology solves the problems of the toxicity and cost. However, although means for altering the stability and substrate specificity of natural-type enzymes are known as described above, concrete means for altering reaction specificities so as to enhance transfer reactions are not known. This is because problems remain unsolved with regard to the structural stability of enzyme themselves or enzyme-substrate complexes, and the mechanisms of enzymatic reactions and relevant factors thereof must be better understood. Furthermore, it seems not only extremely inefficient, but actually impossible to alter enzymes so as to control their reactivity using a trial-and-error substitution method based mainly on information about amino acid sequences, since function and physicochemical characteristics of enzymes are closely related to their three-dimensional structures.

SUMMARY OF THE INVENTION

An object of the present invention is to provide a method to alter an enzyme to enhance its activity for transfer reactions, by a deductive and efficient means taking its three-dimensional structure and reaction mechanism into consideration, and novel neopullulanases prepared according to the method.

A method of altering an enzyme according to the present invention to solve the problems mentioned above is characterized in that a pre-selected specific site of a transferase is treated to increase its hydrophobicity so as to enhance the transfer activity of the enzyme.

The method of altering an enzyme to enhance a transfer reaction according to the present invention is to alter the structure of the enzyme itself so as to partially increase hydrophobicity of the enzyme using various methods such as introducing a new hydrophobic group therein; therefore, the method according to the present invention is safer for industrial use than those using organic solvents, and is thus applicable in various fields such as the food industry.

Furthermore, possible mutants can be very efficiently predicted because the target enzyme is comprehensively analyzed in terms of amino acid sequence, three-dimensional structure, reaction mechanism and the like, and a site to increase hydrophobicity, the kind of hydrophobic groups to be introduced, and the kind of hydrophilic groups to be deleted are deductively determined.

Further, since novel neopullulanases prepared according to the method of enzyme alteration of the present invention have a higher sugar transfer activity than the corresponding native enzyme, more efficient production of branched oligosaccharides by the use of the alpha-1,6 sugar transfer activity of this pullulanase is anticipated.

BRIEF DESCRIPTION OF THE DRAWINGS

In FIG. 1, T.P is neopullulanase (SEQ ID NO:1), R.P is Taka-amylase A (SEQ ID NO:2), + is a residue in the hydrophobic core region of Taka-amylase A, ● is the catalytic site of Taka-amylase A (all numbers below are for those of Taka-amylase A), is a binding site for Taka-amylase A, a helical shape represents the helix site of Taka-amylase A. A contiguous V-shape represents the sheet site of Taka-amylase A and 1 to 4 represents four regions highly conserved in alpha-amylase family enzymes.

In FIG. 2, 21 is the main chain of neopullulanase, 22 is maltotriose (substrate), 23 is a catalytic group, 25 is an oxygen atom and 26 is a carbon atom.

DETAILED DESCRIPTION OF THE PREFERRED EMBODIMENTS

Figure 1C:
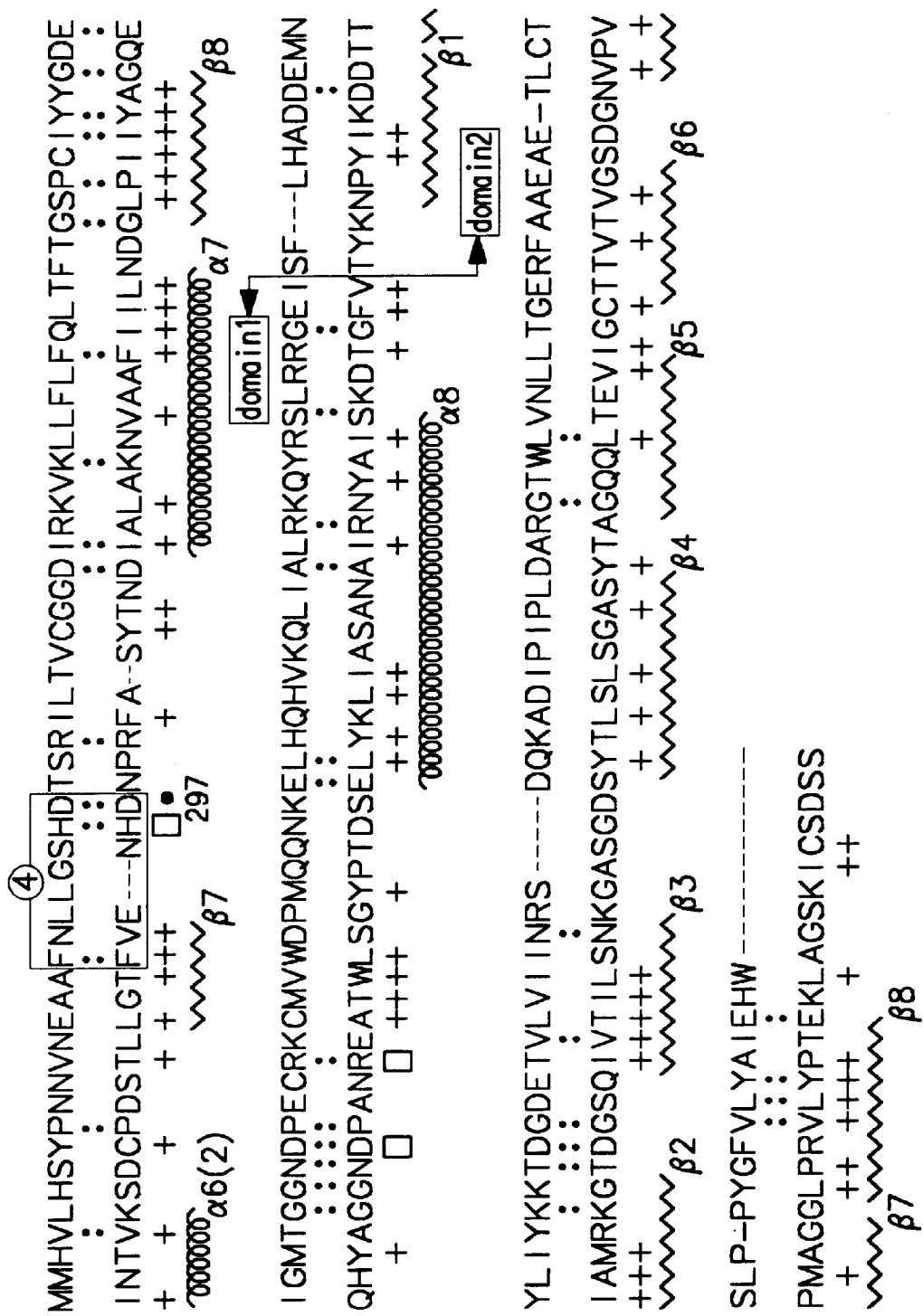
FIG. 1 shows amino acid sequences of neopullulanase and Taka-amylase A aligned for comparison, in which each amino acid residue is represented by one letter style as described below.

The method of altering a transferase according to the present invention is a method to enhance the transfer activity of a transferase, which is characterized in that the transfer activity of the transferase is enhanced by increasing the hydrophobicity of a pre-selected site of the transferase.

In order to increase hydrophobicity of a pre-selected site, for example, either one or more of the following methods are used alone or in combination:

i. Substitution of a group located at the pre-selected site with a hydrophobic group;

ii. Substitution of an amino acid residue located at the pre-selected site with a hydrophobic amino acid residue;

iii. Insertion of a hydrophobic group or a hydrophobic amino acid residue into the pre-selected site, and iv. Deletion of a hydrophilic group or a hydrophilic amino acid residue from a pre-selected site.

"A pre-selected site" is a site in which an increase in its hydrophobicity enhances transfer activity. The site is pre-selected by means described later.

According to the present invention, an enzyme is altered using protein engineering technology so as to have higher transfer reactivity, for example, by introducing a hydrophobic group to change the internal environment of the enzyme, specifically in this case, to increase environmental hydrophobicity. Examples of hydrophobic groups include hydrophobic amino acids as well as alkyl groups or aromatic hydrocarbon groups such as ethyl, propyl and phenyl groups.

The expression "to increase hydrophobicity" as used in the present invention means to decrease hydrophilicity in the case where the selected site is hydrophilic, preferably to change it to be hydrophobic, or to enhance hydrophobicity in the case where the selected site is hydrophobic.

An example of the method of altering an enzyme according to the present invention comprises a first step to specify an active site for the transferase, a second step to specify a site where an acceptor enters near to the active site, a third step to search for a site in which hydrophobicity is to be increased near to the acceptor entering site, and a fourth step to treat the searched site so as to enhance hydrophobicity therein.

An appropriate hydrophobic amino acid or hydrophobic group and site for the introduction are selected by taking the three-dimensional structure and reaction mechanism of the target enzyme into consideration. Also, in the case where a hydrophilic group or hydrophilic amino acid is deleted, the three-dimensional structure and reaction mechanism of the target enzyme are taken into consideration to determine which hydrophilic group or hydrophilic amino acid is to be deleted.

In a method of altering an enzyme according to the present invention, an active site (a catalytic site and a binding site) can be specified based on experimental data on the three-dimensional structure of the target enzyme, if available.

Where such data are not available, the three-dimensional structure is predicted by a molecular modeling method, a cleft which is large enough to accept a substrate molecule is searched for, the amino acid sequence of the site is compared with a homologous protein, and then the active site can be specified by extracting an amino acid, which is assumed to be highly conserved and functionally important from the amino acids which forms the cleft.

A site where the acceptor enters is specified based on experimental data on the three-dimensional structure, if available. Where such experimental data are not available, the entry site is specified by assuming a transfer reaction mechanism based on the enzyme-substrate complex structure obtained by a docking study (a process to search for a maximal interlocation by enzyme-substrate docking simulation using a three-dimensional graphic display).

A site, into which a hydrophobic amino acid is introduced by amino acid substitution or insertion near to the entry site, can be determined, for example, based on the following procedure:

A search is carried out in the same family as the target enzyme to select an enzyme having homology to the target enzyme, but the transfer activity on a different level. Then, the amino acid sequence of the selected enzyme are compared with that of the target enzyme to investigate how increase of hydrophobicity between the corresponding sites of their amino acid sequences contributes for increase in the level of the transfer activity. Regarding the result, the site, into which a hydrophobic amino acid is introduced, can be determined.

In the present invention, a preferable hydrophobic amino acid for insertion into a site to increase hydrophobicity is selected from those which bring high hydrophobicity but do not enlarge its volume as compared to the corresponding site of the target transferase to be altered. Examples of such hydrophobic amino acids include tryptophan, isoleucine, phenylalanine, leucine, valine, glycine, alanine, proline, methionine, tyrosine and cysteine.

Further, examples of transferases to which the method of altering an enzyme according to the present invention can apply include methyltransferase, hydroxylmethyltransferase, formyltransferase, carboxyltransferase, carbamoyltransferase, amidotransferase, enzymes to transfer aldehydes or ketones, acyltransferase, aminoacyltransferase, glycosyltransferase, amino group transferase, oxyimino group transferase, phosphotransferase, pyrophosphoric acid transferase, nucleotide transferase, sulfurtransferase, sulfotransferase and co-enzyme A transferase.

Neopullulanase Y377F is a novel transferase altered according to the present invention, in which tyrosine at position 377 in the amino acid sequence of neopullulanase derived from *Bacillus stearothemophilus* is substituted with phenylalanine.

Neopullulanase S422V is a novel transferase altered according to the present invention, in which serine at position 422 in the amino acid sequence of neopullulanase derived from *Bacillus stearothermophilus* is substituted with valine.

Neopullulanase M375L is a novel transferase altered according to the present invention, in which methionine at position 375 in the amino acid sequence of neopullulanase derived from *Bacillus stearothermophilus* is substituted with leucine.

An ideal method to enhance an enzymatic transfer reaction, which is most efficient and effective in regards to safety and cost, is to alter an enzyme so as to increase the transfer activity indigenous to the enzyme. Protein engineering can be used as a means to alter the enzyme. However, there were the following large questions to be considered:

i. What basic principle should be used to alter the target enzyme?

ii. Which site(s) of the target enzyme should be altered?

iii. What alteration should be incorporated into the site(s)?

The present inventors propose the following methodology to answer the above questions.

A transfer reaction is a reaction to transfer a certain group to a compound, other than water, which acts as an acceptor. More precisely, a part of the starting substrate, a donor, is transferred to the acceptor substrate (an acceptor other than water) which comes later. In contrast, a hydrolytic reaction is a reaction in which water acts as an acceptor. Thus, the two reactions are fundamentally the same in terms of an organic chemical reaction mechanism. However, the activity ratio between transfer reaction and hydrolytic reaction is considerably different even between highly homologous enzymes; some enzymes have extremely high activity only in one of the catalytic reactions. Since these differences are observed between enzymes which seemed to have a common catalytic group, the present inventors predicted that the difference in ratio of the two reactions is attributed to the difference in the internal environment of each enzyme close to the active site. That is, the transfer activity is considered to be high in an enzyme which has a highly hydrophobic environment near to the active site, particularly around the acceptor-entrance site.

Accordingly, it is possible that if a target enzyme is altered by adding appropriate hydrophobicity to an appropriate site of the enzyme to increase the internal hydrophobic environment, the entrance of a water molecule, which is a possible acceptor for a hydrolytic reaction, is hindered whereas entrance of compounds other than water is enhanced, which results in a greater probability of transfer (transfer activity) to the compound other than water. The methods i–iv described above can be used to provide the appropriate hydrophobicity.

In altering enzymes, in general, using this fundamental concept, it is possible to take the following steps to determine which site of hydrophobicity in the enzymes should be increased.

First, the amino acid sequence of the target enzyme (for example native enzyme) to be altered must be clarified. On the basis of this sequence, a homology search is carried out in which an enzyme highly homologous to the target enzyme is searched for from a data base of previously known proteins, so as to predict the functions of the target enzyme. Then, the sequence of the target enzyme is carefully compared with that of the highly homologous known enzyme to find amino acids which presumably construct the catalytic group or binding site.

Subsequently, in order to verify this presumption, for example, experimental introduction of substitution groups can be carried out. Ideally speaking, the three-dimensional structure of the target enzyme is known in this stage, for example, by X-ray crystallography. If for some reason, structural analysis is not possible, the three-dimensional structure is predicted by computer analysis. Furthermore, based on experimental data or presumptive information concerning its enzyme-substrate complex structure with the aid of the three-dimensional graphic display, a site which meets the following conditions is selected as a site or a candidate site where hydrophobicity is to be improved.

(1) A site located near to the active site, in which an acceptor (a compound, including water) can be assumed to enter.

(2) A site located near the active site, in which a substitution associated with a change in hydrophobicity (either increase or decrease) is observed when the amino acid sequence is compared with that of a homologous enzyme.

However, sites which meet the following conditions should be excluded even if they meet the above-mentioned conditions.

(3) A catalytic group and the most important binding site deemed to be essential for binding of a substrate.

(4) A site assumed to be critical to support the overall structure of an enzyme and orientation of the catalytic group.

In introducing a hydrophobic amino acid at a selected site, an amino acid which meets the following conditions is preferably selected.

A. An amino acid which has higher hydrophobicity than an amino acid located in the original (for example native) enzyme at the site of introduction, for example tryptophan, isoleucine, phenylalanine, leucine, valine, glycine, alanine, proline, methionine, tyrosine, cysteine. In this connection, for example, $\pi$ (pi) values (Eur. J. Med. Chem., 18, 369–375, 1983) are used as indices for hydrophobicity of individual amino acids.

B. An amino acid which reduces or maintains the volume of the original (for example native) side chain at the site of introduction.

However, amino acids which are assumed to destroy a hydrogen bond network between an enzyme, substrate and water molecule are excluded even they meet the above-mentioned conditions.

In order to verify the above-mentioned fundamental concept to enhance transfer reaction using neopullulanase, we selected appropriate sites of introduction and the kinds of hydrophobic groups to be introduced on the basis of the above-mentioned conditions and accordingly proceeded to prepare the following three mutants: Y377F mutant (SEQ ID NO: 3) in which the tyrosine residue (Y) at position 377 is replaced by a phenylalanine residue (F), S422V mutant (SEQ ID NO: 4) in which the serine residue (S) at position 422 is replaced by a valine residue (V), and M375L mutant (SEQ ID NO: 5) in which the methionine residue (M) at position 375 is replaced by a leucine residue (L).

Characteristics of the mutant neopullulanases thus obtained were as follows:

Neopullulanase Y377F:

The specific activity decreased but the transfer activity increased.

Neopullulanase S422V:

The specific activity decreased but the transfer activity increased.

Noepullulanase M375L:

The specific activity decreased but the transfer activity increased.

The present invention will be explained more in detail by the following examples.

EXAMPLE 1

In this example, a transfer reaction was enhanced by altering neopullulanase, an enzyme which catalyzes hydrolysis and transfer reactions of sugars, derived from *Bacillus stearothermophilus*.

I. Amino Acid Sequence Analysis

Sequence analysis was carried out to elucidate the relationship between the amino acid sequence of neopullulanase and the mechanism of transfer reaction, from which to find a clue as to transfer enhancement.

First, a homology search was carried out, based on the amino acid sequence of native neopullulanase (SEQ ID NO: 1) using the Protein Data Bank (PDB) at Brookhaven National Laboratory which provides collection of three-dimensional structures of known proteins. Results showed that the amino acid sequence of Taka-amylase A (SEQ ID NO: 2) was highly homologous to neopullulanase as a whole. Taka-amylase A is an enzyme which hydrolyzes sugars in the same manner as does neopullulanase but catalyzes a transfer reaction only to a minimal extent. Amino acid sequences of Taka-amylase A and neopullulanase were aligned. Results are shown in FIG. 1. In FIG. 1, T.P is neopullulanase, R.P is Taka-amylase A, + is a residue in the hydrophobic core region of Taka-amylase A, ● is the catalytic site of Taka-amylase A (all numbers below are for those of Taka-amylase A), □ is a binding site for Taka-amylase A, a helical shape represents the helix site of Taka-amylase A. A contiguous V-shape represents the sheet site of Taka-amylase A and 1 to 4 represent four regions highly conserved in alpha-amylase family enzymes. This FIG. 1 suggests that a unique domain structure comprising 120 amino acid residues is present at the N-terminal of neopullulanase and indicates that most of insertion/deletion sites found in both sequences maintain complete secondary structures and that in Taka-amylase A, all amino acids which are probable catalytic groups and some amino acids which are a probable binding site are conserved. Consequently, regarding the fundamental structure which is considered to be important for the enzymatic function, it is predicted that the fundamental structure of neopullulanase, except for the N-terminal domain, is highly homologous to that of Taka-amylase A.

Further, it was experimentally confirmed that Asp328, Glu357 and Asp424 are catalytic groups of neopullulanase and that the transfer and hydrolytic reactions are catalyzed in the same active center.

II. Prediction of the Three-dimensional Structure

The three-dimensional structure of neopullulanase has not been elucidated experimentally. Therefore, prediction of the structure was carried out in order to elucidate the relationships between the three-dimensional structure and the mechanism of transfer reaction, from which to find a clue as to transfer enhancement.

The three-dimensional structure of neopullulanase was predicted based on the homology modeling method with reference to sequence alignment with Taka-amylase A and the 3-D structure of Taka-amylase A. Further, the structure of maltoheptaose, one of the substrates, was predicted by connecting seven units of alpha- D-glucose via alpha-1,4 linkages so as to form an overall left-handed helical structure.

Furthermore, a completed neopullulanase and a substrate were exhibited on a three-dimensional graphic display. The substrate was docked into the active cleft of the enzyme while continuously monitoring the relative orientation of catalytic groups and glucosidic bonds to be cleaved by the catalytic action as well as three-dimensional repulsion between the enzyme and substrate (this is hereinafter referred to as docking study).

Finally, the structure of a neopullulanase-sub-strate complex was predicted. The resultant model is shown in FIG. 2.

Figure 2:
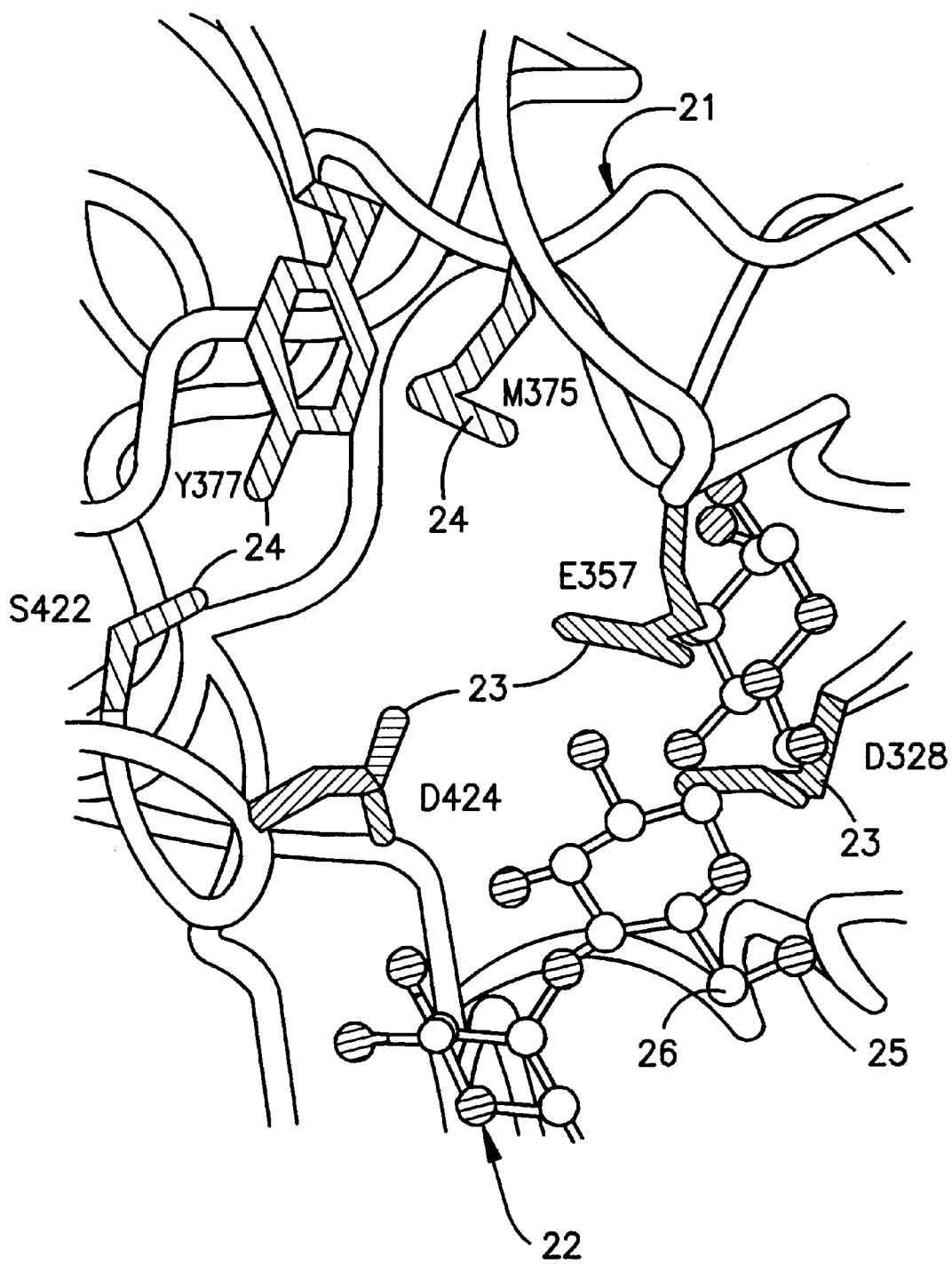
FIG. 2 shows the predicted structure of a neopullulanase-substrate complex.

In FIG. 2, 21 is the main chain of neopullulanase, 22 is maltotriose (substrate), 23 is a catalytic group, 25 is an oxygen atom and 26 is a carbon atom. Since maltotriose is used as a substrate in this Example, the sugar in FIG. 2 is also maltotriose.

The amino acid sequence analysis and three-dimensional structure prediction were carried out using an expert system, commercially available BIOCES [E] (NEC Co., Ltd.), for protein engineering and drug designing. Details of this system are described in Japanese Patent Application No. 216344/1992; L,aid-Open No. 44323/1994.

III. Prediction of Mechanism of Transfer Reaction

Figure 3:
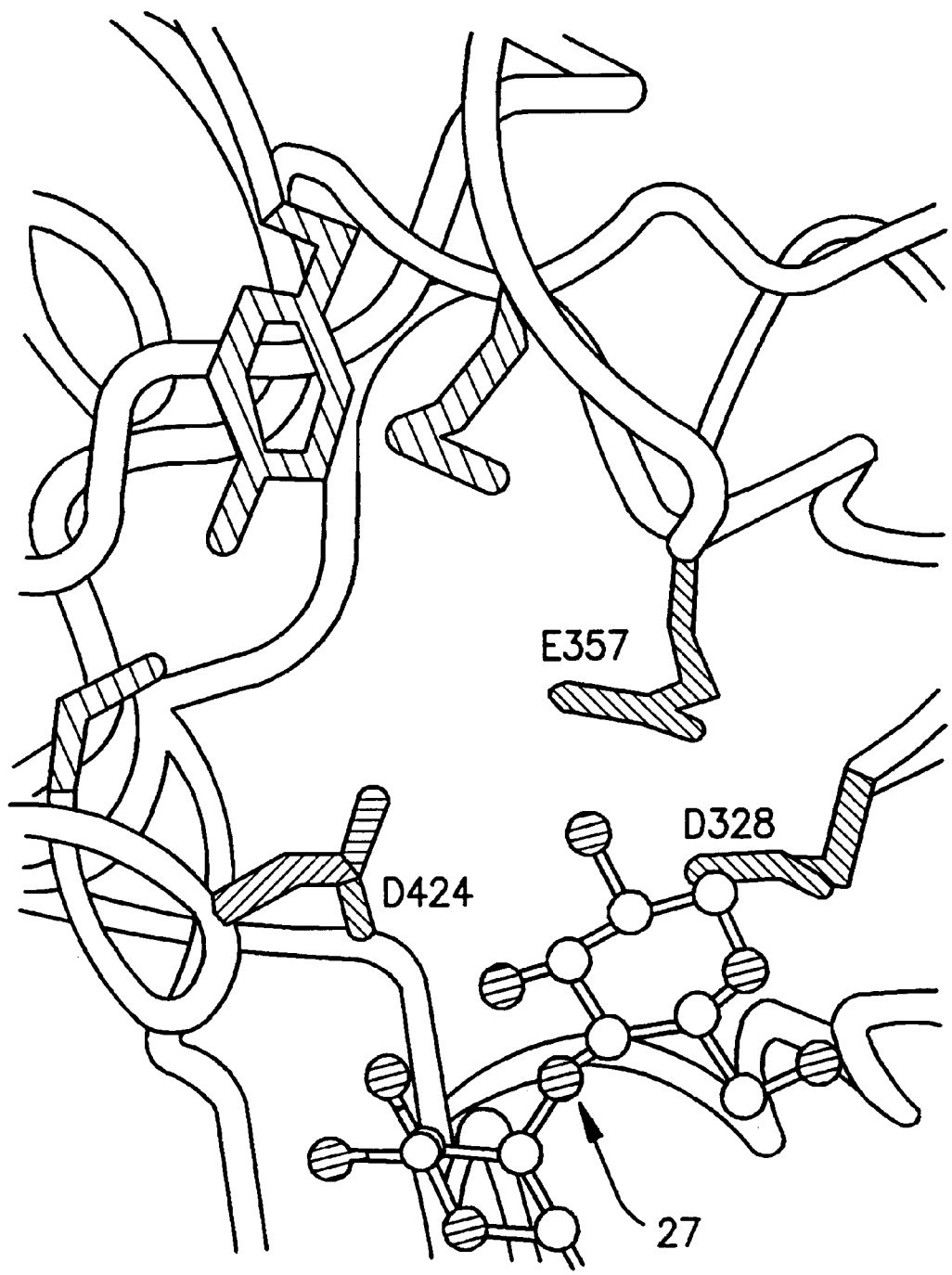
FIG. 3 shows a structure similar to FIG. 2, in which a carbonium cation intermediate 27 is stabilized by Asp328 (D328)

The enzyme-substrate complex structure in FIG. 2 shows that the catalytic group Asp328 (D328) is located in the lowest part (bottom part) of the active cleft so as to support the glucosidic bond from the beta side (H-1 atom side). From this, we made a reaction model in which a carbonium cation intermediate 27, which is considered to be generated as a result of an attack of a proton of Glu357 (E357) to a glucosidic bond, is stabilized by Asp328 (D328) as illustrated in FIG. 3, then acceptors (in this case, water 28 and maltotriose 29) enter from the Asp424 (D424) side (alpha side) which is spacious and also in contact with the solvent, as shown in FIG. 4, and finally the intermediate is transferred to one of these acceptors to form maltopentaose 30, as shown in FIG. 5.

IV. Selection of Hydrophobic Groups for Introduction

Figure 4:
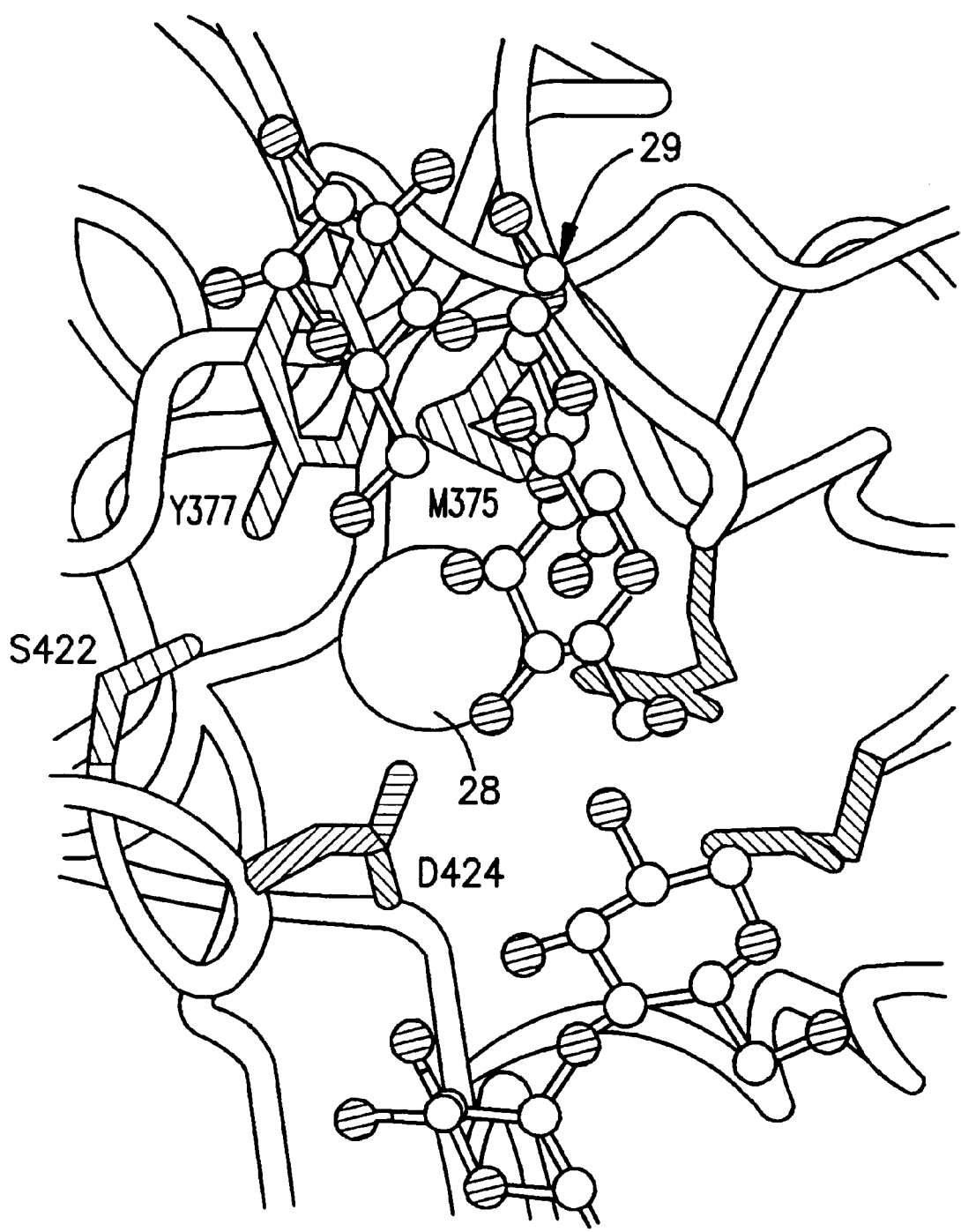
FIG. 4 shows the FIG. 3 structure after water 28 and maltotriose 29 have entered from the Asp424 (D424) side.
Figure 5:
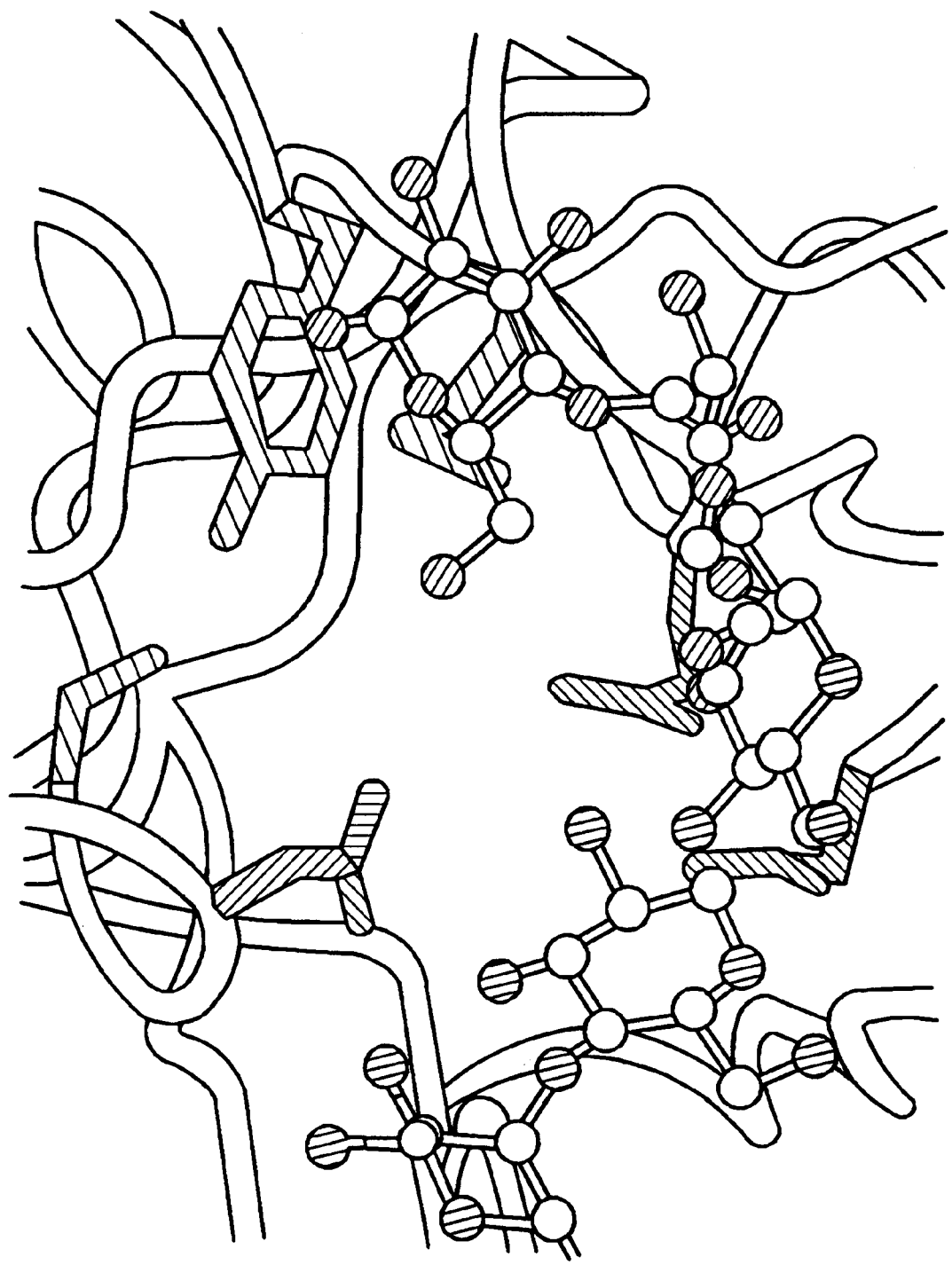
FIG. 5 shows the FIG. 4 structure after the intermediate is transferred to one of the acceptors, to form maltopentaose 30.

A site adjacent to Asp424 (D424), through which acceptors enter, was searched according to the above-mentioned reaction model with reference to the three-dimensional structure shown in FIG. 4. As a result, three positions (target sites to be altered 24), namely position 377, position 422 and position 375 were selected.

Position 377 is a tyrosine residue (Y) in the native enzyme. On the other hand, results of the amino acid sequence analysis with Taka-amylase A revealed that this site is conserved by tyrosine (Y) also in Taka-amylase A. Given that the transfer activity of Taka-amylase A is much lower than that of neopullulanase, it is necessary to further increase hydrophobicity in this site. Thus, a phenylalanine residue (F) was selected to be introduced because it meets this requirement and the volume of the side chain is reduced since one OH group disappears.

Position 422 is a serine residue (S) in the native enzyme. In this case, since the volume of the side chain of the serine residue is considerably small, a valine residue (V) was selected for introduction because it is considered to not only minimize a volume increase; but also increase hydrophobicity.

Position 375 is a methionine residue (M) in the native enzyme, while this site is replaced by a leucine residue (L) in Taka-amylase A. Since average apparent volumes for a methionine residue (M) and a leucine residue (L) are almost the same, a leucine residue (L) was selected as a hydrophobic group to be introduced in this site, which corresponds to an alteration to a Taka-amylase-type enzyme.

V. Preparation of Wild-type and Mutant Neopullulanases

An ordinary wild-type (synonymous with natural-type) enzyme was prepared as follows. Recombinant plasmid pUNP129 was introduced in a commercially available strain of *Escherichia coli* TG-1; the resultant cells were cultured at 37° C. in 100 ml of L medium (containing 100 micrograms/ml ampicillin) in a 500-ml volume Sakaguchi flask, after several hours when turbidity of the culture measured at 660 nm using et spectrometer reached close to 0.6, 0.1 mM IPTG (isopropyl-beta-D-thiogalactopyranoside) was added as an inducer for enzyme production and the incubation was continued at 30° C. overnight. The cells were harvested, washed and then ultrasonically disrupted. The resultant centrifuged supernatant was purified by ion exchange column chromatography, by hydrophobic column chromatography and again by ion exchange column chromatography until a single band was shown by electrophoresis.

Figure 6:
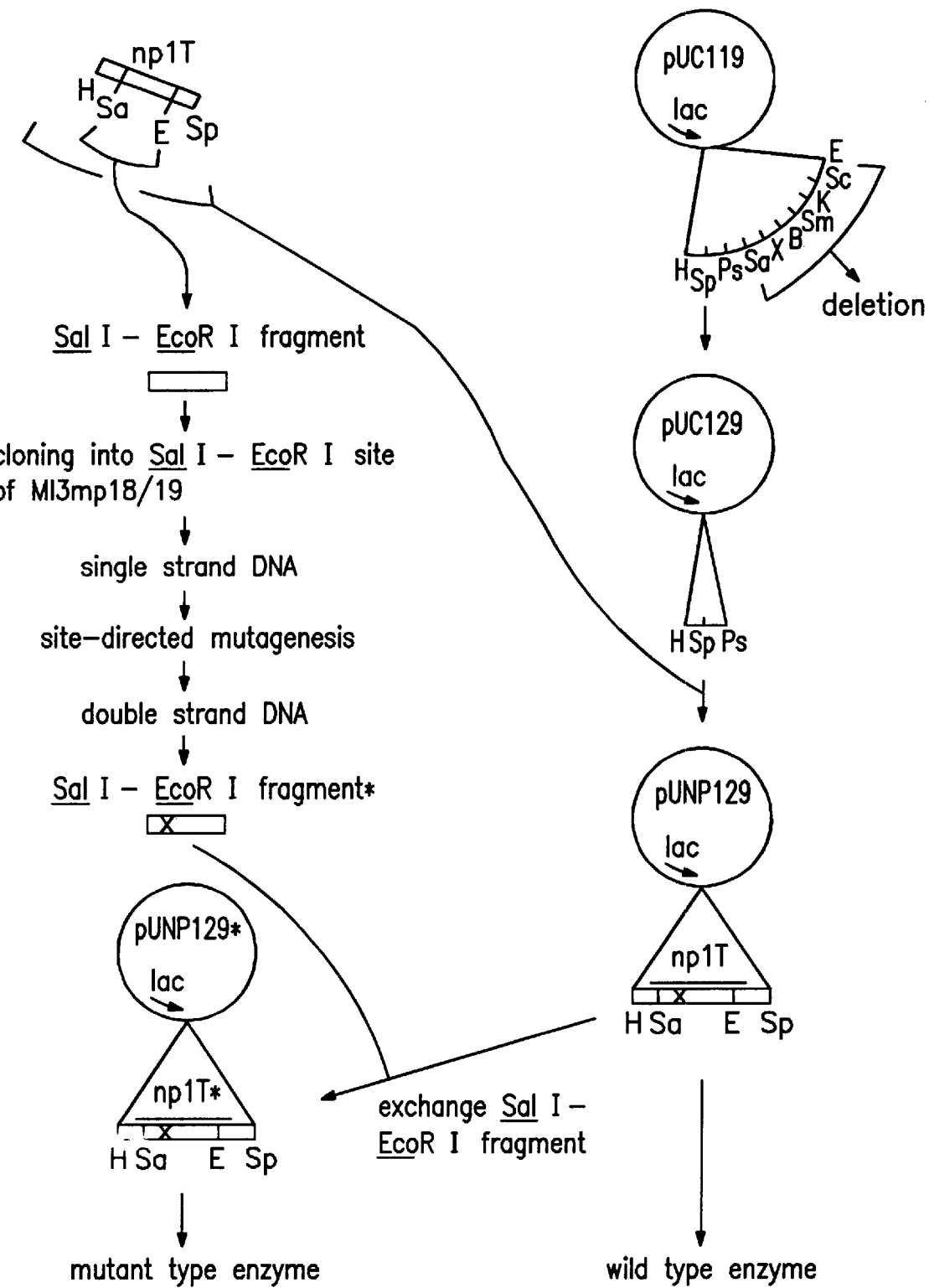
FIG. 6 shows the steps for introducing site-directed mutation in neopullulanase and construction of a plasmid for enzyme production.

The recombinant plasmid pUNP129 was constructed according to the method illustrated in FIG. 6. In FIG. 6, H, Sp, Ps, Sa, X, B, Sm, K, Sc and E are clearing sites for restriction enzymes HindIII, SphI, PstI, SalI, XbaI, BamHI, SmaI, KpnI, SacI and EcoRI, respectively, and * means mutant-type. First, a commercially available vector plasmid pUC119 was cleaved with restriction enzymes SalI and EcoRI, the termini were repaired with DNA polymerase I and then the resultant blunt ends were ligated to produce plasmid pUC129in which SalI-EcoRI fragment, the multi-cloning site of pUC119, was deleted.

A chromosomal DNA was prepared according to the method of Imanaka et al. (Imanaka et al., J. Bacteriol., 147, 776–786, 1981) from *Bacillus stearothermophilus* TRS40 strain (deposited at National Institute of Bioscience and Human- Technology, (old name: Fermentation Research Institute), Agency of Industrial Science and Technology, Ministry of International Trade and Industry, 1-3, Higashi 1-chome, Tsukuba, Ibaraki, Japan, under the deposit number FERM P- 9606).

Separately, from this, based on the nucleotide sequence of a known neopullulanase (Kuriki and Intanaka, J. Gen. Microbiol., 135, 1521, 1989), sequences having 20 to 30 base pairs were selected upstream from the initiation codon and downstream from the termination codon, and oligonucleotides corresponding to these sequences were synthesized in the usual manner. In order to make the subsequent steps easy, sequences which can be recognized by appropriate restriction enzymes were added to these oligonucleotides. The oligonucleotides thus obtained (primers 1 and 2) have the following sequences:

Primer 1 (SEQ ID NO: 6):
    5' TTTAAGCTTTTTTCTACTGAATTTG 3'
Primer 2 (SEQ ID NO: 7):
    5' TTTGCATGCAAAGAACGCTCGGG 3'

PCR (polymerase Chain Reaction) was carried out using the above-mentioned two primers, and chromosomal DNA from the TSR40 strain cells obtained as above, by the ordinary method (Molecular Cloning: A Laboratory Manual, 2nd Ed. 1989). From the resultant amplified products, a DNA fragment having the target structural gene of neopullulanase was obtained using electrophoresis. A restriction map of the fragment was made and compared with that of the gene of a known neopullulanase to confirm the acquisition of the target DNA fragment.

Subsequently, the DNA fragment containing the neopullulanase structural gene was treated with restriction enzymes HindIII and SphI, and the resultant HindIII-SphI DNA fragment was inserted into the HindIII-SphI site of pUC129, which was previously prepared, to construct pUNP129. In this plasmid., the neopullulanase structural gene is located downstream of the lac promoter and its expression is directed by the promoter.

In order to introduce site-directed mutation, the SalI-EcoRI fragment was obtained by cleaving the HIndIII-SphI DNA fragment with restriction enzymes SalI and EcoRI, and then cloned into the SalI-EcoRI site in the multi-cloning site of commercially available phage M13mp18 or M13mp19 and a single strand DNA was prepared for use as a template for site-directed mutation. (FIG. 6). The preparation of the single-strand DNA and the procedure for site-directed mutation were carried out using a commercially available oligonucleotide-directed in vitro mutagenesis system (Amersham) according to the accompanying instructions. The SalI-EcoRI fragment in which the mutation had been introduced was exchanged with the SalI-EcoRI fragment of pUNP129 in ordinary manner to construct pUNP129*. Subsequently, transformation was carried out in an ordinary manner using the pUNP129*. Cells of *Escherichia coli* TG-1 carrying this mutant pUNP129 were cultured and the mutant-type enzyme was purified in the same manner as for the wild-type enzyme producing strain.

Vi. Characteristics of Mutant Neopullulanases 0.02 U each of the wild-type enzyme and mutant enzyme was added to a 10 w/v % maltotriose solution (10 mM phosphate buffer, pH 6.0) and the reaction was carried out at 40° C. One unit of enzyme activity was defined as the amount of enzyme which generates one micromole of glucose in one minute when the reaction was carried out at 40° C. in a solution containing 10 w/v % maltotriose and enzyme (50 mM phosphate buffer, pH 6.0).

Reaction products were analyzed by high performance liquid chromatography. Glucose and maltoee are hydrolytic products, while isomaltose and oligosaccharides with a degree of polymerization higher than that of maltotetraose are counted as products of transfer reactions. Thus, the amount and distribution cf the products in hydrolytic reaction and transfer reactions by the wild-type enzyme and the mutant enzymes were compared at the point where the starting substrate, maltotriose, was reduced by 40%.

REFERENCE EXAMPLE 1

Furthermore, additional mutants Y377S and Y377D in which the tyrosine residue (Y) at position 377 is replaced by a serine residue (S) and an aspartic acid residue(D), respectively, were prepared and characterized. As shown in Table 1, the transfer activity decreased and the hydrolytic activity increased in both mutant enzyme reactions. This revealed that the hydrolytic activity of the native enzyme increased when the enzyme was altered to enhance its hydrophilic environment by introducing a new hydrophilic group in an appropriate site.

TABLE 1

| Enzyme | Rate of reaction products | | |
|---|---|---|---|
| | Hydrolytic reaction (A) | Transfer reaction (B) | Ratio (B/A) |
| Wild-type | 22.9 | 17.1 | 0.747 |
| Mutant  Y377F | 19.1 | 20.9 | 1.09 |
| S422V | 20.0 | 20.0 | 1.00 |
| W375L | 20.5 | 19.5 | 0.951 |
| Y377D | 23.8 | 16.2 | 0.681 |
| Y377S | 23.2 | 16.8 | 0.724 |

The results in Table 1 show that the amount of target transfer product (target product) from the Y377F and S422V mutant enzymes were increased by about 20% as compared with that from the wild-type enzyme. This increase eases subsequent steps such as concentration, isolation and purification in the preparation of the target product from the mixture with other products. Further, it has been reported that a daily dose of about 10 g of isomaltooligosaccharide in human showed a bowel-controlling action (Kohmoto, et al., Agric. Biol. Chem., 55, 2157–2159, 1991). Assuming that an effective daily dose for the bowel-controlling action is 10 grams, while the wild-type enzyme produces enough product for a five-day period (50 g), the mutant enzyme according to the present invention produces enough product for a 6 day-period (60 g, increase by 20%) under the same conditions. This difference verifies the advantage of the mutant strain according to the present invention over the wild-type strain.

In the Examples above, alterations were described on a glycosyltransferase, neopullulanase, derived from *Bacillus stearothermophilus*; however, the present invention is not limited to this particular transferase but it is universally applicable to any transferase including methyltransferase, hydroxylmethyltranferase, formyltransferase, carboxyltransferase, carbamoyltransferase, amidotransferase, enzymes to transfer aldehydes or ketones, acyltransferase, aminoacyltransferase, glycosyltransferase, amino group transferase, oxyimino group transferase, phosphotransferase, pyrophosphoric acid transferase, nucleotide transferase, sulfurtransferase, sulfotransferase and co-enzyme A transferase.

---

What is claimed is:

1. A method to enhance to the transfer activity of a transferase with an acceptor group other than water by increasing the hydrophobicity of either its active site or its acceptor site, or both its active and acceptor sites, by making one or more amino acid sequence alterations, said method comprising:
  a) specifying the three-dimensional structure of said transferase, with and without a substrate, by applying data from X-ray crystallography analysis of the transferase or by homology modeling with data from X-ray crystallography analysis of a similar transferase;
  b) specifying the mode of action of said transferase;
  c) specifying an active site for the transferase comprising a catalytic site and a binding site;
  d) specifying an acceptor site where an acceptor enters near to the active site;
  e) identifying one or more amino acid positions where hydrophobicity may be increased within or adjacent to said acceptor site; and
  f) making one or more amino acid sequence alterations at said amino acid positions identified within or adjacent to said acceptor site selected from the group of alterations consisting of
    1) substitution(s) of (a) naturally-occurring amino acid(s) at said position or positions with (a) more hydrophobic amino acid(s),
    2) insertion of (a) hydrophobic amino acid(s) at said position or positions,
    3) deletion of (a) hydrophobic amino acid(s) at said position or positions,
  wherein (a)n amino acid(s) selected for said substitution(s) or said insertion(s) produces, by comparison with the hydrophobicity and volume at said sites in the native transferase, an increased hydrophobicity in or near said active and/or acceptor site(s) with no increase in volume.

2. The method according to claim 1, wherein the transferase has hydrolysis activity.

3. The method according to claim 1, wherein a site in which hydrophobicity is to be increased is decided by selecting a side chain or a part of said chain which is located in an amino acid in said acceptor site which can be changed so as to increase the hydrophobicity of the amino acid.

4. The method according to claim 1, wherein the hydrophobic amino acid is tryptophan, isoleucine, phenylalanine, leucine, valine, glycine, alanine, proline, methionone, tyrosine or cysteine.

5. The method according to claim 1, wherein the transferase is methyltransferase hydroxylmethyltransferase, formyltransferase, carboxyltransferase, carbamoyltransferase, anidotransferase, enzymes to transfer aldehydes or ketones, acyltransferase, aminoacyltransferase, glycosyltrasferase, amino group transferase, oxymino group transferase, phosphotransferse, pyrophosphoric acid transferase, nucleotide transferase, sulfurtransferase, sulfotransferase or co-enzyme A transferase.

6. The method according to claim 2 wherein the increase in hydrophobicity resulting from an amino acid sequence alteration prevents entry of water molecules subject to hydrolysis into the active site thus enhancing the transfer activity of the transferase.

7. A method to enhance to the transfer activity of a transferase with an acceptor group other than water by increasing the hydrophobicity of either its active site or its acceptor site, or both its active and acceptor sites, by making one or more amino acid sequence alterations, said method comprising:
  a) specifying the three-dimensional structure of said transferase, with and without a substrate analog compound, by applying data from X-ray crystallography analysis of the transferase in a stable complex with said substrate analog compound and without said compound;
  b) specifying the mode of action of said transferase;
  c) specifying an active site for the transferase comprising a catalytic site and a binding site;
  d) specifying an acceptor site where an acceptor enters near to the active site;
  e) identifying one or more amino acid positions where hydrophobicity may be increased within or adjacent to said acceptor site; and
  f) making one or more amino acid sequence alterations at said amino acid positions identified within, or adjacent to, said acceptor site selected from the group of alterations consisting of
    1) substitution(s) of (a) naturally-occurring amino acid(s) at said position or positions with (a) more hydrophobic amino acid(s),
    2) insertion of (a) hydrophobic amino acid(s) at said position or positions, and
    3) deletion of (a) hydrophilic amino acid(s) at said position or positions.

8. The method according to claim 7, wherein the transferase has hydrolysis activity.

9. The method according to claim 7, wherein a site in which hydrophobicity is to be increased is decided by selecting a side chain or a part of said chain which is located in an amino acid in said acceptor site which can be changed so as to increase the hydrophobicity of the amino acid.

10. The method according to claim 7, wherein the hydrophobic amino acid is tryptophan, isoleucine, phenylalanine, leucine, valine, glycine, alanine, proline, methionine, tyrosine or cysteine.

11. The method according to claim 7, wherein the transferase is methyltransferase hydroxylmethyltransferase, formyltransferase, carboxyltransferase, carbamoyltransferase, anidotransferase, enzymes to transfer aldehydes or ketones, acyltransferase, aminoacyltransferase, glycosyltransferase, amino group transferase, oxyimino group transferase, phosphotransferase, pyrophosphoric acid transferase, nucleotide transferase, sulfurtransferase, sulfotransferase or co-enzyme A transferase.

12. The method according to claim 8, wherein the increase in hydrophobicity resulting from an amino acid sequence alteration prevents entry of water molecules subject to hydrolysis into the active site thus enhancing the transfer activity of the transferase.

* * * * *